US009588118B2

(12) United States Patent
Goren et al.

(10) Patent No.: US 9,588,118 B2
(45) Date of Patent: Mar. 7, 2017

(54) DEVICES FOR PERFORMING COLORIMETRIC ASSAY WITH PLUCKED HUMAN HAIR

(71) Applicant: Follea International Ltd., Central (HK)

(72) Inventors: Andy Ofer Goren, Newport Beach, CA (US); John McCoy, Downey, CA (US); Daniel Hafid, Newport Beach, CA (US)

(73) Assignee: Follea International, Irvine, CA (US)

( * ) Notice: Subject to any disclaimer, the term of this patent is extended or adjusted under 35 U.S.C. 154(b) by 515 days.

(21) Appl. No.: 14/247,196

(22) Filed: Apr. 7, 2014

(65) Prior Publication Data

US 2014/0335537 A1    Nov. 13, 2014

Related U.S. Application Data

(63) Continuation-in-part of application No. 13/245,783, filed on Sep. 26, 2011, now Pat. No. 8,691,518.

(60) Provisional application No. 61/386,451, filed on Sep. 24, 2010.

(51) Int. Cl.
*G01N 31/00* (2006.01)
*G01N 33/53* (2006.01)
*G01N 33/573* (2006.01)
*C12Q 1/48* (2006.01)

(52) U.S. Cl.
CPC ............. *G01N 33/573* (2013.01); *C12Q 1/48* (2013.01); *G01N 2333/46* (2013.01); *G01N 2333/91194* (2013.01); *G01N 2800/04* (2013.01); *G01N 2800/20* (2013.01); *G01N 2800/52* (2013.01)

(58) Field of Classification Search
CPC ................ C12Q 1/48; G01N 2333/46; G01N 2333/91194; G01N 2800/04; G01N 2800/20; G01N 2800/52; G01N 33/573
See application file for complete search history.

(56) References Cited

U.S. PATENT DOCUMENTS

| | | | |
|---|---|---|---|
| 4,849,347 A | 7/1989 | Familletti et al. | |
| 5,760,315 A | 6/1998 | Verheijden et al. | |
| 5,958,946 A | 9/1999 | Styczynski et al. | |
| 6,075,005 A | 6/2000 | Lurie | |
| 8,691,518 B2 * | 4/2014 | Tam .................. | C12Q 1/48 435/15 |
| 8,758,993 B2 | 6/2014 | Goren et al. | |
| 2011/0212167 A1 | 9/2011 | Ali et al. | |
| 2014/0023618 A1 | 1/2014 | Goren et al. | |
| 2014/0335537 A1 | 11/2014 | Goren et al. | |

FOREIGN PATENT DOCUMENTS

| | | |
|---|---|---|
| CA | 2233961 A1 | 4/1997 |
| SE | EP 1307181 B1 | 11/2005 |
| WO | 2011/109459 A2 | 9/2011 |

OTHER PUBLICATIONS

Baker et al., "Minoxidil sulfation in the hair follicle," Skin Pharmacol , 7:335-339 (1994).
Buhl et al., "Minoxidil sulfotransferase activity influences the efficacy of Rogaine® topical solutions (TS)—enzyme studies using scalp and platelets," The Journal of Investigative Dermatology, 7:534 (1994).
Dooley et al., "Localization of minoxidil sulfotransferase in rat liver and the outer root sheath of anagen pelage and vibrissa follicles," The Society for Investigative Dermatology, Inc., 96:65-70 (1991).
Hebbring et al., "Sulfotransferase gene copy number variation: pharmacogenetics and function," Cytogenet and Genome Research, 123:205-210 (2008).
Yu et al., "Copy number variation in sulfotransferase isoform IAI (SULTIAI) is significantly associated with enzymatic activity in Japanese subjects," Pharmacogenomics and Personalized Medicine, 6:19-24 (2013).
Goren, A., et al., "Therapeutic Hotline: Novel enzymatic assay predicts minoxidil response in the treatment of androgenetic alopecia," Dermatologic Therapy, vol. ••, 2013, 4 pages.
Office Action (Restriction) in U.S. Appl. No. 13/843,908, mailed Dec. 26, 2014.
Anderson et al., Sulfation of minoxidil by multiple human cytosolic sulfotransferases., Chem Biol Interact. (1998), vol. 109(1-3), pp. 53-67.
Frame et al., A simple Colorimetric Assay for Phenotyping the Major Human Thermostable Phenol Sulfotransferase (SULT1A1) Using Platelet Cytosols, Drug Metabolism and Disposition (2000), vol. 28, pp. 1063-1068.
Falany, C. N. et al., "Sulfation of Minoxidil by Human Liver Phenol Sulfotransferase," Biochemical Pharmacology, vol. 40, No. 5, 1990, pp. 1027-1032.
Johnson, G. A. et al., "Sulfation of Minoxidil Platelet Sulfotransferase," Clinica Chimica Acta, vol. 169, 1987, pp. 217-228.
Buhl et al. "Minoxidili Sulfate is the Active Metabolite that Stimulate Hair Follicles", Journal of Investigative Dermatology, 1009, vol. 95, pp. 553-557.
PCT International Search Report and Written Opinion in International Application No. PCT/US12/57399, mailed on Feb. 21, 2013.
PCT Invitation to Pay Additional Fees and, Where Applicable, Protest Fee, in International Application No. PCT/US12/57399, mailed on Nov. 29, 2012.
Office Action in U.S. Appl. No. 13/245,783, USPTO, Alexandria, VA, dated Aug. 8, 2013.
Randall et al. "Mechanism of Androgen Action in Cultured Dermal Papilla Cells Derived from Human Hair Follicles with Varying Responses to Androgens In Vivo", 1992. J. Invest Dermatol. 98:86S-91S.

(Continued)

*Primary Examiner* — Lisa Cook
(74) *Attorney, Agent, or Firm* — Buchanan Ingersoll & Rooney PC

(57) ABSTRACT

Apparatuses are disclosed for performing calorimetric assays with plucked human hair using a device adapted for that purpose. This device may include a transparent reaction vessel connected via a capillary tube to a burst pack, and connected via another capillary tube to a funnel, into which a plucked human hair may be placed.

19 Claims, 6 Drawing Sheets

(56) References Cited

OTHER PUBLICATIONS

Giulani et al. 2010. "Rutin efficacy in hair loss" J. Invest Dermatol. 130 Suppl 1, p. S102, #607.
Brozic et al. "Inhibitors of Aldo-Keto Reductases AKR1C1-AKR1C4", 2011. Current Med. chem 18:2554-2565.
Halim et al. "Imaging Induction of Cytoprotective Enzymes in Intact Human Cells: Coumberone, a Metabolic Reporter for Human AKR1C Enzymes Reveals Activation by Panaxytriol, an Active Component of Red Ginseng" 2008. JACS 130:14123-14128.
Eicheler et al. "5α-Reductase activity in the human hair follicle concentrates in the dermal papilla" 1998. Arch. Dermatol. Res. 290:126-132.
Rodriguez et al. "Expanding the use of fluorogenic enzyme reporter substrates to imaging metabolic flux changes: the activity measurement of 5α-steroid reductase in intact mammalian cells." 2010. ACS Chemical Biol. 5:1045-1052.
PCT International Search Report and Written Opinion in International Application No. PCT/US2012/060321, International Search Authority, Alexandria, VA, mailed Mar. 29, 2013.
Office Action in U.S. Appl. No. 13/652,463, USPTO, Alexandria, VA, dated Jul. 25, 2013.

\* cited by examiner

DEVICES FOR PERFORMING COLORIMETRIC ASSAY WITH PLUCKED HUMAN HAIR

CROSS-REFERENCE TO RELATED APPLICATIONS

This application is a continuation-in-part of U.S. patent application Ser. No. 13/245,783, filed on Sep. 26, 2011 now U.S. Pat. No. 8,691,518, entitled "Systems and Methods for Predicting Response to Minoxidil for the Treatment of Androgenetic Alopecia," which is incorporated herein by reference in its entirety, which claims priority to U.S. Provisional Application Ser. No. 61/386,451, filed on Sep. 24, 2010, titled "System and Method for Predicting Response to Minoxidil for the Treatment of Androgenetic Alopecia Based on a Rapid Colorimetric Assay."

This application is related to U.S. application Ser. No. 14/247,196, filed on Apr. 7, 2014, entitled "Systems and Methods for Predicting Response to Minoxidil for the Treatment of Androgenetic Alopecia," to inventors Phillip Y. Tam and Andy Ofer Goren, which is incorporated by reference herein in its entirety.

TECHNICAL FIELD

The present disclosure relates generally to a device and method for conducting a colorimetric chemical assay using plucked human hair.

BACKGROUND

Point-of-care (POC) diagnostic devices are commonly employed to assay biomarkers of different human health or disease states. For example, a pregnancy test is a lateral flow POC that reports the presence of the beta subunit of human chorionic gonadotropin (hCG) in urine. hCG is a biomarker produced by the trophoblastic cells of the fertilized ova. As such, the presence of hCG in urine can be reported to the user of the device by a chemical reaction that produces a visible color or change in the device indicating that the user is pregnant. Many different POC devices are currently available commonly using bodily fluids as substrates (e.g., blood, urine, or saliva). Each device has similar characteristics: they are portable, handheld and typically made of plastic. Most POC can only be used once and are considered disposable.

BRIEF SUMMARY

Described herein are embodiments including point-of-care devices for measuring one or more biomarkers contained in one or more plucked human hair(s). In addition, a devices are described for measuring sulfotransferase enzyme activity in one or more plucked human hair(s) for the purpose of predicting the effectiveness of the drug minoxidil for the treatment of a particular individual's hair loss.

In one embodiment, a device is provided for performing a colorimetric assay. This device may comprise an encasement, and a cavity within the encasement comprising a burst pack comprising a first reagent. The burst pack may be situated such that it may be burst by pressure from one or more human fingers. The first reagent may react with the follicle of a human hair to produce a change in a measurable optical property of the reagent. The device may further comprise a transparent reaction vessel within the encasement comprising a reaction chamber, and a first capillary tube opening on one end to the reaction chamber, and opening on another end to a funnel. The funnel may open to the atmosphere external to the reaction vessel. The device may further comprise a second capillary tube providing a fluid connection between the cavity and the reaction chamber.

In one embodiment, a device such as that described above may be used as follows: A sample may be obtained from a human subject, comprising a hair that has been plucked from the human subject, the hair comprising a follicle at one end. The hair may be placed, follicle-end first, into the funnel of the device, and situating the follicle such that it is within reaction chamber. The burst pack may be broken, and a color change of the material may be measured in the reaction vessel.

In another embodiment, a device may comprise an encasement and a reaction vessel within the encasement comprising a reaction chamber. A first capillary tube may open on one end to the reaction chamber, and open on another end to a funnel. The funnel may open to the atmosphere external to the reaction vessel. The first capillary tube may have a diameter between about 0.25 ml and about 2.5 ml. The device may further comprise a first reagent which reacts with the follicle of a human hair to produce a change in a measurable property of the reagent.

BRIEF DESCRIPTION OF THE DRAWINGS

The accompanying drawings, which are incorporated into this specification, illustrate one or more embodiments of the inventions disclosed herein. Together with the detailed description, these serve to explain the principles and example implementations of these inventions. The drawings are illustrative only. What is depicted therein may be adapted based on the text of the specification or the common knowledge within this field.

In the drawings, where like reference numerals refer to like reference in the specification.

DETAILED DESCRIPTION

Examples are described herein in the context of a point-of-care diagnostic device for measuring biomarkers from plucked human hair. The following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same reference indicators will be used to the extent possible throughout the drawings and the following description to refer to the same or like items.

In the interest of clarity, not all of the routine features of the implementations described herein are shown and described. In the development of any such actual implementation, numerous implementation-specific decisions must be made in order to achieve the developer's specific goals, such as compliance with application- and business-related constraints, and that these specific goals will vary from one implementation to another and from one developer to another. Moreover, such a development effort might be complex and time-consuming, but would nevertheless be a routine undertaking of engineering for those of ordinary skill in the art having the benefit of this disclosure.

The terms "exemplary" is used exclusively herein to mean "serving as an example, instance or illustration." Any embodiment described herein as "exemplary" is not necessarily to be construed as preferred or advantageous over other embodiments.

Figure 1:
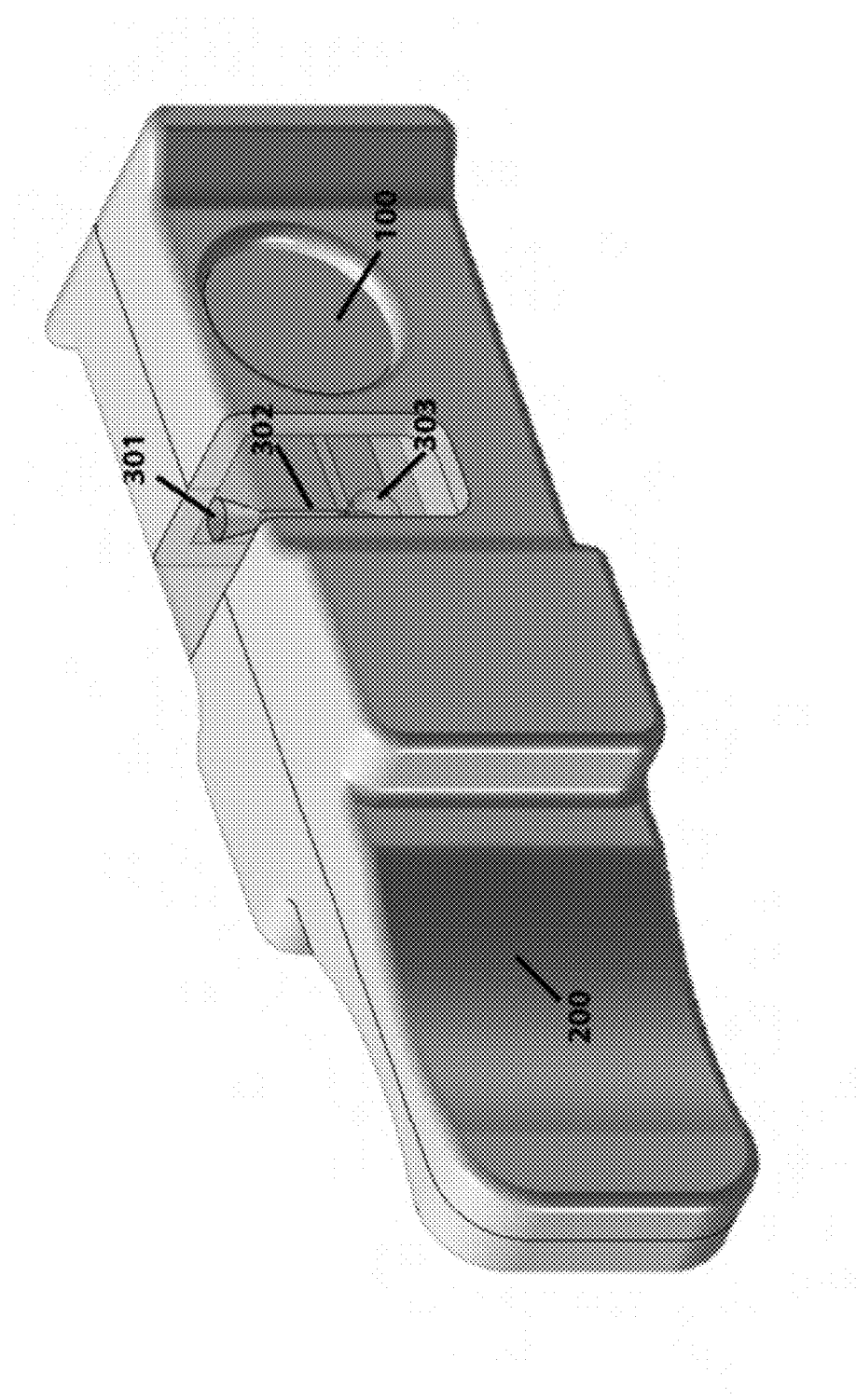
FIG. 1 is a drawing of a device for measuring biomarkers contained in plucked human hair.

FIG. 1 is a schematic diagram of a device for measuring biomarkers contained in plucked human hair. The device is constructed of three parts, a burst-pack (100) that contains a chemical solution that will be delivered to the bulb of a plucked human hair, a reaction vessel (300) cast in clear plastic or other material that will hold and position a plucked human hair, and an encasement (200) that holds together 100 and 300 in a convenient manner, such that a test may be performed by delivering the chemistry contained in 200 to the reaction vessel 300.

Figure 2:
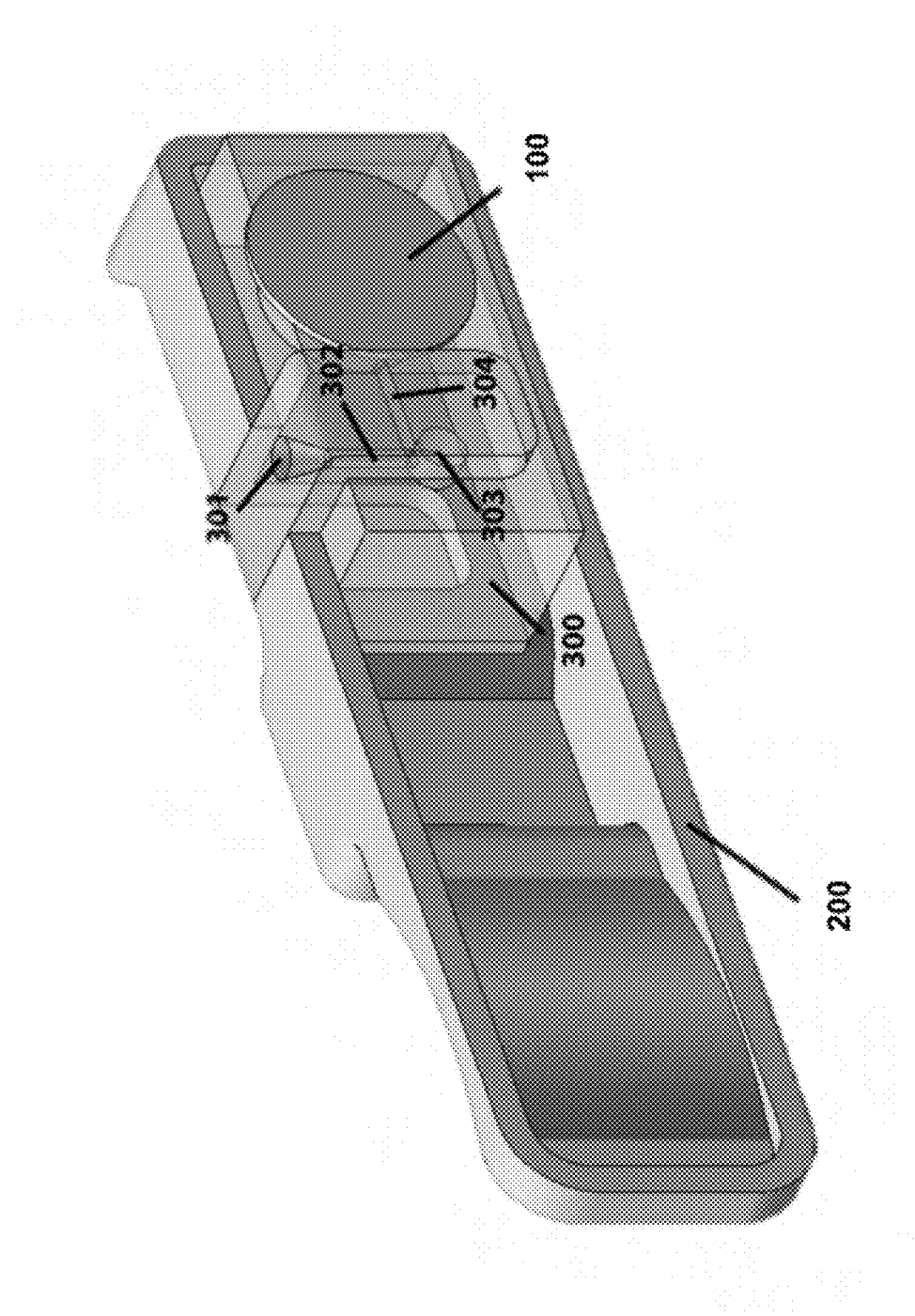
FIG. 2 is a drawing showing a cut-away view of a device for measuring biomarkers contained in plucked human hair.

FIG. 2 is a cutaway view of the device in FIG. 1. In the described device a plucked human hair is inserted into the device by the user such that the hair bulb, containing cells of the outer root sheath, inner root sheath, medulla, germinative cells, and dermal papilla are placed in the reaction chamber at 303. To aid guidance of the hair bulb to the reaction chamber (303), a funnel (301) connects to a capillary (302), which then connects to the reaction chamber at 303. Any number of chemistries may be delivered to a hair bulb placed in the reaction chamber 303 via a capillary 304. In one embodiment, the diameter of capillary 302 may be slightly larger than the diameter of the largest normal human hairs in the human population. In another embodiment, the diameter may be between about 0.25 mm to about 2.5 mm. In another embodiment, the diameter may be approximately 1 mm.

In another embodiment, the capillary at 304 may be omitted. With such an arrangement a chemistry may be placed directly into the reaction chamber 303 either by a dropper or other such means. The device may also be manufactured such that a chemistry was already stored in the reaction chamber 303. In that case, a user may then simply add hair.

In another embodiment, the device of FIG. 1 may include a button to start an assay test. The button may in one example include an electronic device that would supply electric current to a light emitting diode (LED) as an indicator that the test has begun. In another embodiment, a visible timer may be provided to count down the time for the reaction to come to completion.

Figure 3:
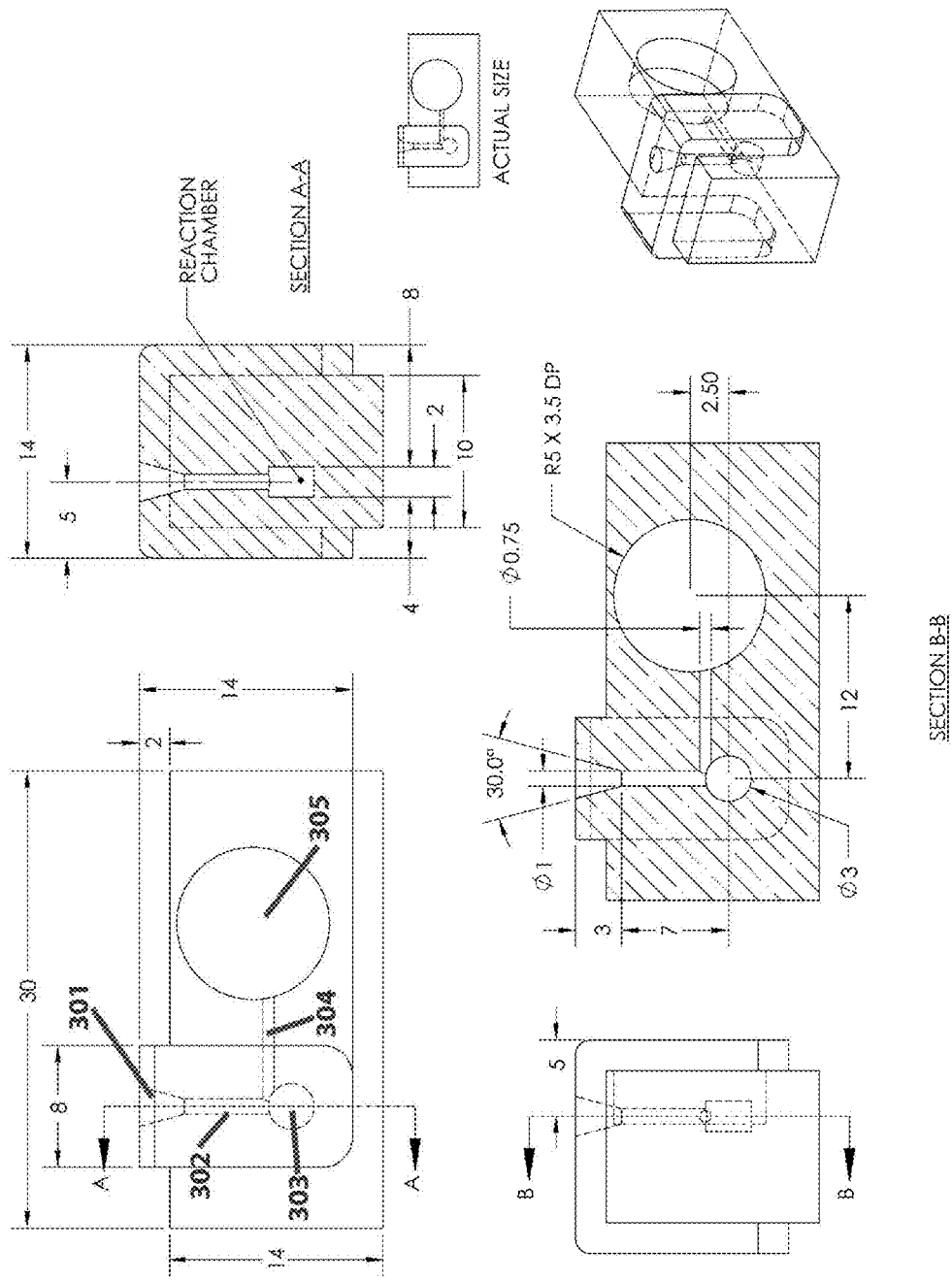
FIG. 3 is a schematic drawing of a reaction vessel for measuring biomarkers contained in plucked human hair.

FIG. 3 is a technical drawing, depicting a prototype version of the reaction vessel 300. Descriptive measurements in millimeters are provided for the depicted funnel (301), capillary (302), reaction chamber (303), capillary (304) and depression (305) for mounting burst-pack (100) containing chemistry to be delivered. The reaction vessel is made of a transparent material so that a color change produced in the reaction chamber (303) is visible to the user of the device.

In another embodiment, a built in reader may substitute for the visual detection schemes described above. In one example, a physical measurement such as an optical absorbance may be used as the first input in the device to report a result to the user. For example, a spectrophotometer reading of the reaction chamber 303 may be used and report to the user an optical absorbance.

In another embodiment, a device may be built in such a manner that it would be compatible with a digital camera, such as a digital camera in a mobile device or mobile computer terminal. The digital camera or reader may act as a built in reporter and would substitute for the visual detection schemes described earlier. In such a device, a physical measurement, for example, an optical absorbance may be interpreted by a computer algorithm in a mobile device and report a result to the user. For example, a digital camera reading of the reaction chamber 303 could be used as a first input to report a color change in the reaction chamber 303.

In another embodiment, the reaction vessel 300 or some other part of the device may be coated with a material that would display a plus or minus sign to report a test result to the user.

Figure 4:
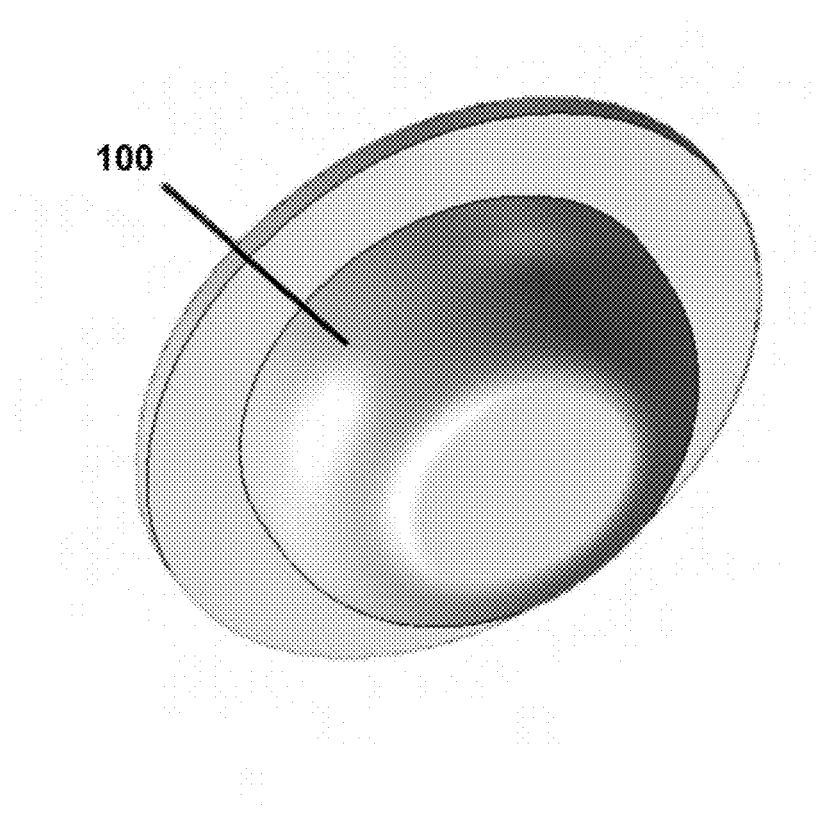
FIG. 4 is a drawing showing an enlarged view of a burst pack.

FIG. 4. is a depiction of a burst-pack containing a chemistry to be delivered to the reaction chamber. A burst-pack is a sealed container, which may for example be made of a clear film, plastic, or aluminum foil pouch with a burstable internal seal that can flow a liquid after it is broken by mechanical force, usually by pressing with a finger. The burst pack may also have a button mounted above it, to start the test when the button is pressed.

Figure 5:
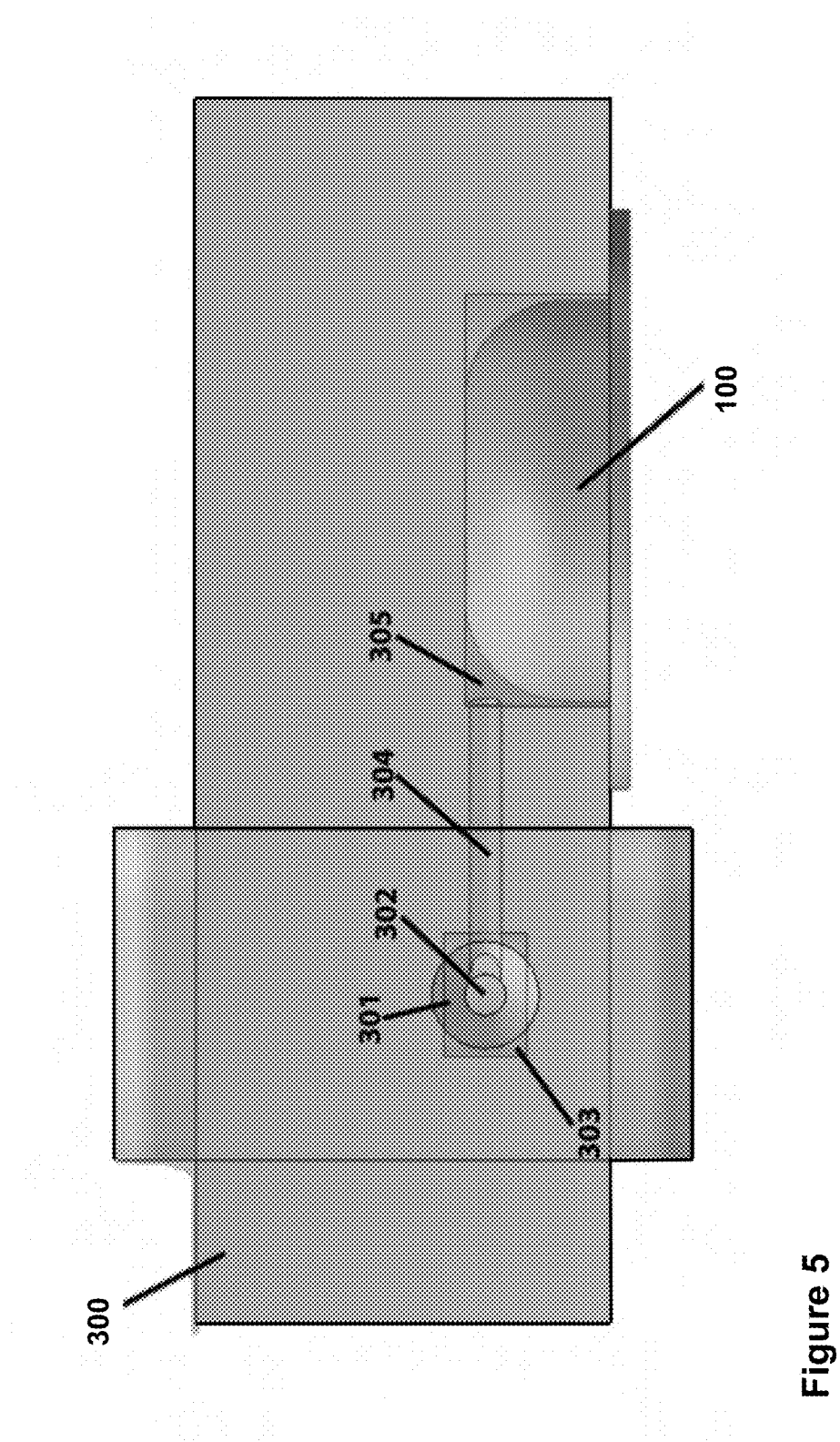
FIG. 5 is a drawing showing a top view of a reaction vessel, and a burst pack.

FIG. 5 is a top view of the reaction vessel (300) depicting alternate views of the funnel (301), capillary (302), reaction chamber (303), capillary (304), depression for burst-pack (305) including a mounted burst-pack (100).

Figure 6:
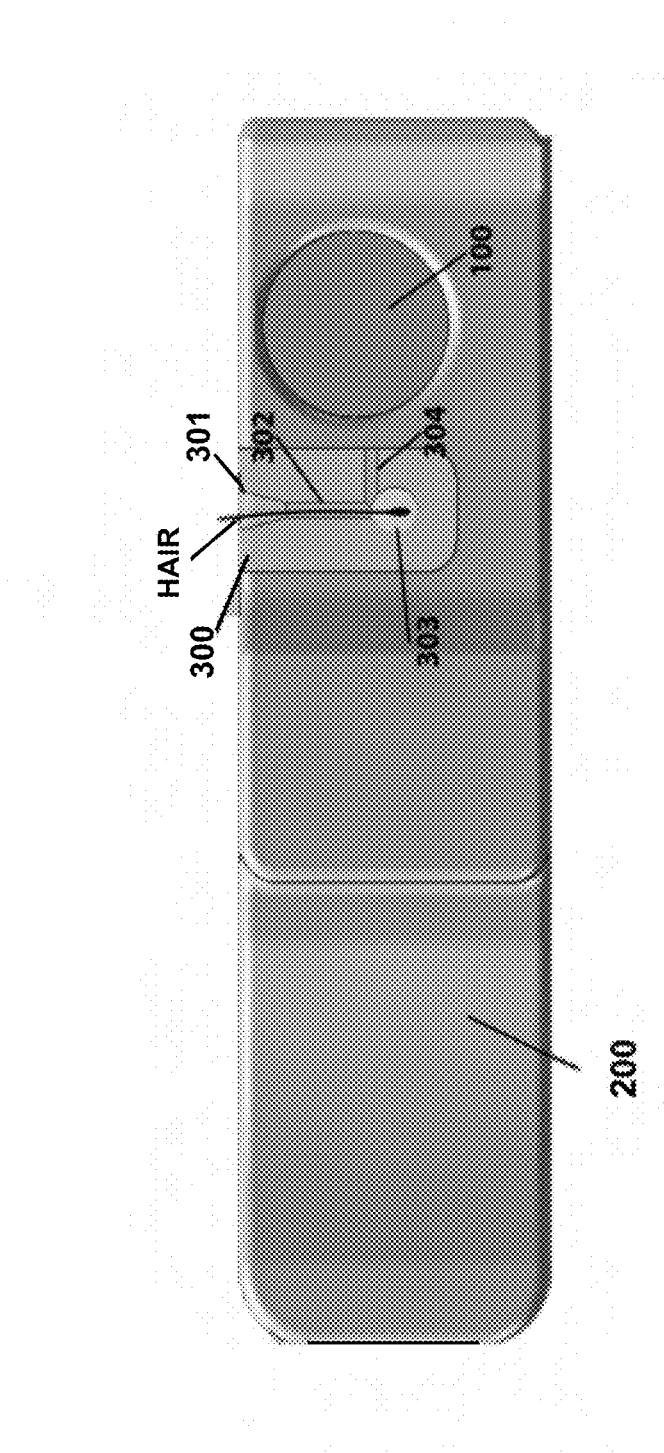
FIG. 6 is a drawing of a device containing a plucked human hair.

FIG. 6 is a front view of the device depicted in FIG. 1 shown with an inserted human hair. The hair is positioned so that the bulb is placed in the reaction chamber (303)

The point-of-care device as described can be used to assay biological content (e.g. DNA, RNA, protein or lipid) of a plucked human hair. In one embodiment of the present device an individual would pluck a hair or several hairs and place the hair(s) into the device funnel 301 through capillary 302, so that the bulb of all hairs were positioned in the reaction chamber 303. Once the hairs are positioned in 303 the individual would press firmly on the burst-pack 100 releasing a chemical assay solution into a sealed depression 305, which would flow the assay solution through capillary 304 into the reaction chamber 303. Once submersed in the assay solution, the endogenous biological material contained in the hair would react with the assay solution and produce a color that would be readable by the individual. Depending on the chemical composition of the assay solution a change in color of the solution would indicate to the individual a particular state of health or disease.

In one embodiment, surfaces of parts of the reaction chamber, such as reaction chamber 303, capillaries 302 and/or 304, or funnel 301, may be coated with one or more reagents. For example, in an anti-body test, such surfaces might be coated with an antibody using antibody coating or attachment means known in the art.

In one embodiment, devices as described above may be used for the predictive assessment of an individual's likelihood to respond favorably to the drug minoxidil. Minoxidil requires biochemical activation by minoxidil sulfotransferase to form the active minoxidil sulfate metabolite. The exact mechanism of action for minoxidil based treatment of androgenetic alopecia is not completely understood. However, in vitro studies have demonstrated that minoxidil sulfate is the active metabolite of minoxidil. Response to minoxidil for the treatment of androgenetic alopecia has been associated with differences in scalp sulfotransferase activity. Therefore, a subject with a high level of minoxidil sulfotransferase activity will generate more minoxidil sulfate, and therefore will likely have a good response to minoxidil for the treatment of androgenetic alopecia. On the other hand, a subject with a low level of minoxidil sulfotransferase activity will not generate much minoxidil sulfate, and will likely have a poor response to minoxidil for the treatment of androgenetic alopecia.

Clinical trials with minoxidil for the treatment of androgenetic alopecia have shown statistically significant results for maintenance and growth of hair. Several studies have demonstrated the level of minoxidil sulfotransferase activity is significantly greater in patients responding to minoxidil for the treatment of androgenetic alopecia. As described herein, the assessment of hair re-growth is based on one or more of the following parameters: patient self assessment, physician assessment using a standardized scale, global photography assessment, hair diameter measurement, average hair length measurement, average hair diameter measurement, and hair weight measurements. The current inventions provide a method of using biochemical variations in minoxidil sulfotransferase activity as a drug response marker for minoxidil treatment of androgenetic alopecia. Based on the minoxidil sulfotransferase activity level, the method disclosed herein allows a physician or the patient to select the appropriate treatment and dosage thereof for the treatment of androgenetic alopecia.

In accordance with one approach described herein, a patient's hair follicle sample may be obtained. Preferably, at least two hair follicles may be obtained, so that if only one is analyzed, there will be at least one backup if needed.

In one example, the assay solution in a device as described herein may contain about 50 mM phosphate buffer (pH8), about 5 mM potassium p-nitrophenyl sulfate, about 20 µM adenosine 3',5'-diphosphate, about 100 µM minoxidil, and about 5 mM $MgCl_2$. The combination of above mentioned assay solution with the present invention may constitute a point-of-care diagnostic of an individual's likely response to the drug minoxidil using a plucked human hair. This specific assay solution for detecting minoxidil response develops a yellow color for positive responders of minoxidil, which would be visible through the transparent reaction vessel 300. A decal may in one embodiment be added to the present invention to help users determine useful levels of color change and correlate color change with an individual's likely response to the drug minoxidil.

In one embodiment this reaction may take place in a container other than those specifically described herein. For example, it may be a transparent container with a lid or other opening in which the hair follicle samples may be inserted. In one non-limiting example, the total amount of liquid in the assay container may be about 0.2 ml.

As part of the above reaction, it is understood that in the presence of minoxidil sulfotransferase activity, p-nitrophenyl sulfate is converted to the colorimetric p-nitrophenolate.

The reaction may in one embodiment be mixed and then incubated for approximately 4 to 16 hours at 37° C. depending on the number of hair follicles used in the assay. Mixing may be by any mixing means known in the art, including shaking the container. Where a shorter incubation time is required for a greater number of hair follicles. In one embodiment, an assay that uses one hair follicle may be incubated for approximately 16 hours. In another embodiment, an assay that uses two hair follicles may be incubated for approximately four hours.

After sample incubation, the reaction may be stopped by addition of about 1/10 volume of approximately 0.25 M Tris-HCl buffer, pH 8.7, and mixed. The pH may vary, in one embodiment between 8.5 to 9.0. Especially if the assay is performed or sold as part of a kit, the basic buffer may be provided as a separate container for pouring into the assay reaction container. In another embodiment, the basic buffer may be provided in a pre-loaded syringe, to be injected into the main reaction container at the appropriate time, either by manually pushing a plunger, or by some automatic or computerized control.

The absorbance at about 405 nm may then be read with a spectrophotometer or compared to a reference color card with a range of intensities corresponding to minoxidil sulfotransferase activity. Patients with a relatively high level of sulfotransferase activity will have a relatively strong colorimetric readout, resulting in a relatively significant color change. In comparison, patients with a relatively low level of sulfotransferase activity will have a relatively weak colorimetric readout, and correspondingly a relatively minimal color change. Patients with a strong colorimetric assay response would be expected to respond to minoxidil for hair re-growth or retention. Whereas, patients with a weak colorimetric assay response would be expected to have a poor response to minoxidil.

In yet another embodiment, the result from a patient's hair follicle colorimetric assay is used to determine an optimal treatment regime. Including, modifying the concentration and/or frequency of minoxidil therapy to suit the patient's minoxidil sulfotransferase activity. Furthermore, if a patient is unlikely to respond to minoxidil, finasteride may be recommended as an alternative to minoxidil.

In one embodiment, a method may be performed which includes collection of a hair follicle sample from a subject. Then, the hair follicle sample may be coded with a unique identifier, for instance to protect privacy and facilitate handling. The hair follicle sample may be analyzed as described above. The analysis may be performed in one embodiment using the colorimetric assay described herein. The results of the analysis may then be provided to the subject or to the caregiver of the subject. The results of the analysis, each associated with its unique identifier, may in one example be transmitted to a computer system that may include a Web-based server that is accessible, with proper authentication for instance using the unique identifier, by the subject or caregiver. The result, in addition to providing an indication of the likelihood that the patient will respond to 2%, 5% or greater minoxidil for the treatment of androgenetic alopecia, may also include a prediction of the dosage required and daily frequency of treatment by comparing a patient's minoxidil sulfotransferase activity level to a reference database. In other embodiments, other indicators relating to the assay may be provided.

In one embodiment, a sample of hair follicle from a subject may be sent to a lab. An analysis of the sample in accordance with one or more of the afore-mentioned procedures may then be conducted. Results of the analysis may for example be compared with a database to generate an indication of the likelihood that the patient will respond to minoxidil for the treatment of androgenetic alopecia. The database may be dynamic in nature, continuously updated for statistical adaptation based on past minoxidil treatment and response thereto, so that the database can adapt, or learn, from the patient pool and treatments over time, and in this manner become a better predictor of the likelihood of responders to the drug treatment. The database, or other entity or circuit or module capable of the adaptive scheme herein described, may reside in computer system or separately therefrom. The outcome of the comparison and analysis may be forwarded to the subject's or caregiver's computer system, for example electronically by way of a network, such as the Internet. Alternatively or in addition, the outcome of the comparison and analysis can be stored on a server for accessing remotely by the subject or caregiver following proper authentication that may require reference to the unique identifier to preserve privacy.

It may also be possible to use a neural network to implement the above-described systems and methods, to in one embodiment predict the likelihood that the patient will respond to minoxidil for the treatment of androgenetic alopecia based on the patient's minoxidil sulfotransferase activity profile. According to such an approach, for predicting the likelihood of response to the drug treatment can include (a) constructing an N-layer neural network, and (b) training the neural network with a data set of patients' outcomes to treatment with minoxidil for androgenetic alopecia along with the patients' minoxidil sulfotransferase activity profiles, (c) obtaining a hair follicle sample from the subject (d) generating a minoxidil sulfotransferase activity profile from the sample, the profile being a function of values associated with a prescribed set of minoxidil sulfotransferase activity levels; (e) inputting the subjects minoxidil sulfotransferase activity profile into the neural network; (f) obtaining a value or set of values from the neural network indicative of the patient's expected outcome (respondent) to the drug treatment at a single or multiple dosages; and (g) providing the patient the drug treatment at the recommended dosage.

The specific examples above relating to minoxidil and sulfotransferase activity ais not intended to be limiting as the present inventions are amenable to any colorimetric assay of biological material contained in human hair. For example colorimetric assays for micro-inflammation, finasteride response, etc.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

The invention claimed is:

1. A device for performing a colorimetric assay comprising:
an encasement;
a cavity within the encasement comprising a burst pack comprising a first reagent, the burst pack situated such that it may be burst by pressure from one or more human fingers, wherein the first reagent reacts with the follicle of a human hair to produce a change in a measurable optical property of the reagent;
a transparent reaction vessel within the encasement comprising a reaction chamber;
a first capillary tube opening on one end to the reaction chamber, and opening on another end to a funnel, said funnel opening to the atmosphere external to the reaction vessel; and
a second capillary tube providing a fluid connection between the cavity and the reaction chamber.

2. The device of claim 1, wherein at least a portion of the reaction chamber is coated with a second reagent.

3. The device of claim 2, wherein the second reagent is an antibody.

4. The device of claim 1, further comprising a plucked human hair that has been inserted through the funnel, such that a hair follicle of the plucked human hair is situated within the reaction chamber.

5. The device of claim 1, wherein the first capillary tube has a diameter between about 0.25 mm and about 2.5 mm.

6. The device of claim 1, wherein the first reagent is an aqueous solution comprising:
about 3 to about 7 mM p-nitrophenyl sulfate; and
about 0.07 to about 0.13 mM minoxidil; and
about 15 to about 25 µM adenosine 3',5'-diphosphate (PAP) or adenosine 3'-phosphate,5'-phosphosulfate (PAPS).

7. The device of claim 6, wherein the concentration of adenosine 3',5'-diphosphate (PAP) or adenosine 3'-phosphate,5'-phosphosulfate (PAPS) is about 20 µM; the concentration of p-nitrophenyl sulfate is about 5 mM; and the concentration of minoxidil is about 0.1 mM.

8. The device of claim 6, wherein the first reagent further comprises:
about 30 to about 70 mM sodium or potassium phosphate buffer (pH about 6.5 to about 8.0); and
about 3 to about 7 mM magnesium chloride.

9. A system for performing a colorimetric assay, comprising:
the device of claim 1;
a spectrophotometer comprising a sample port shaped to accommodate said device, wherein the light source is oriented to pass light through the transparent reaction vessel.

10. A method for performing a colorimetric assay using the device of claim 1, comprising:
obtaining a sample from a human subject, comprising a hair that has been plucked from the human subject, the hair comprising a follicle at one end;
placing the hair, follicle-end first, into the funnel of the device, and situating the follicle such that it is within the reaction chamber;
breaking the burst pack; and
measuring a color change of material in the reaction vessel.

11. The method of claim 10, wherein the calorimetric assay is to measure minoxidil sulfotransferase activity in the sample, further comprising:
generating an activity value indicative of the minoxidil sulfotransferase activity level in the sample, wherein the activity value correlates with the color change;
comparing the activity value to one or more standardized activity values, each standardized activity value representing either high or low expected minoxidil response for hair re-growth or retention for a class of patients including the subject, thereby producing an indication of either high or low expected minoxidil response for hair re-growth or retention for the subject at a particular dosage of minoxidil; and
presenting the indication to the human subject.

12. The method of claim 10, wherein the step of measuring comprises:
taking a digital photograph of the reaction vessel;
running an application on a computer device which compares a color value obtained from the digital photograph in a visual area of the digital photograph corresponding to the reaction vessel with a standard color value.

13. A device for performing a colorimetric assay comprising:
   an encasement;
   a reaction vessel within the encasement comprising a reaction chamber;
   a first capillary tube opening on one end to the reaction chamber, and opening on another end to a funnel, said funnel opening to the atmosphere external to the reaction vessel, wherein the first capillary tube has a diameter between about 0.25 ml and about 2.5 ml;
   a first reagent which reacts with the follicle of a human hair to produce a change in a measurable property of the reagent.

14. The device of claim 13, further comprising:
   a cavity within the encasement comprising a burst pack comprising the first reagent, the burst pack situated such that it may be burst by pressure from one or more human fingers; and
   a second capillary tube providing a fluid connection between the cavity and the reaction chamber.

15. The device of claim 14, further comprising a button which bursts the burst pack when pressed.

16. The device of claim 13, further comprising:
   an electrical current source;
   a switch;
   a visual display connected to the electrical current source when the switch is activated, and configured to provide a visual indication when a reaction between a human hair inserted into the reaction chamber hair and the first reagent has begun.

17. The device of claim 16, further comprising an electronic timer connected to the electrical current source when the switch is activated, and configured to provide a visual indication on the display when a predefined period of time has elapsed.

18. The device of claim 13, wherein a portion of the reaction vessel is coated with an indicator material arranged in the shape of a human-readable visual indicator, wherein the indicator material is activated to provide a visual indication by said change in the measurable property of the reagent.

19. A method for performing a colorimetric assay using the device of claim 13, comprising:
   obtaining a sample from a human subject, comprising a hair that has been plucked from the human subject, the hair comprising a follicle at one end;
   placing the hair, follicle-end first, into the funnel of the device, and situating the follicle such that it is within the reaction chamber;
   reacting the follicle with the first reagent for a predetermined period of time; and
   measuring said measurable property of the reagent.

* * * * *